(12) United States Patent
Majercak et al.

(10) Patent No.: US 7,794,487 B2
(45) Date of Patent: Sep. 14, 2010

(54) REDUCED DEPLOYMENT FORCE DELIVERY DEVICE

(75) Inventors: David C. Majercak, Stewartsville, NJ (US); Jin S. Park, Parsippany, NJ (US); Diana M. Sanchez, Bernardsville, NJ (US)

(73) Assignee: Cordis Corporation, Miami Lakes, FL (US)

( * ) Notice: Subject to any disclaimer, the term of this patent is extended or adjusted under 35 U.S.C. 154(b) by 721 days.

(21) Appl. No.: 11/190,369

(22) Filed: Jul. 27, 2005

(65) Prior Publication Data

US 2006/0025844 A1 Feb. 2, 2006

Related U.S. Application Data

(60) Provisional application No. 60/591,950, filed on Jul. 28, 2004.

(51) Int. Cl.
*A61F 2/06* (2006.01)
(52) U.S. Cl. ...................................................... 623/1.11
(58) Field of Classification Search ................ 623/1.11, 623/1.13
See application file for complete search history.

(56) References Cited

U.S. PATENT DOCUMENTS

| | | | |
|---|---|---|---|
| 4,580,568 A | 4/1986 | Gianturco | |
| 4,655,771 A | 4/1987 | Wallsten | |
| 4,665,771 A | 5/1987 | Mitchell | |
| 4,665,905 A | 5/1987 | Brown | |
| 4,732,152 A | 3/1988 | Wallsten et al. | |
| 4,733,665 A | 3/1988 | Palmaz | |
| 4,925,445 A | 5/1990 | Sakamoto | |
| 4,950,227 A * | 8/1990 | Savin et al. | 623/1.12 |
| 5,201,757 A * | 4/1993 | Heyn et al. | 606/198 |
| 5,445,646 A * | 8/1995 | Euteneuer et al. | 606/198 |
| 5,662,703 A * | 9/1997 | Yurek et al. | 623/1.12 |
| 5,690,644 A * | 11/1997 | Yurek et al. | 623/1.11 |
| 5,741,326 A * | 4/1998 | Solovay | 623/2.25 |
| 5,776,140 A * | 7/1998 | Cottone | 623/1.11 |
| 5,810,871 A * | 9/1998 | Tuckey et al. | 606/198 |
| 5,817,101 A * | 10/1998 | Fiedler | 623/1.11 |
| 5,843,090 A * | 12/1998 | Schuetz | 623/1.11 |
| 5,957,974 A * | 9/1999 | Thompson et al. | 623/1.13 |
| 6,059,813 A * | 5/2000 | Vrba et al. | 606/198 |
| 6,139,572 A * | 10/2000 | Campbell et al. | 623/1.11 |
| 6,210,429 B1 * | 4/2001 | Vardi et al. | 623/1.11 |
| 6,221,097 B1 * | 4/2001 | Wang et al. | 623/1.11 |
| 6,280,412 B1 * | 8/2001 | Pederson et al. | 604/103.07 |

(Continued)

FOREIGN PATENT DOCUMENTS

WO 96/32078 A1 10/1996

(Continued)

OTHER PUBLICATIONS

International Search Report re: PCT/US2005/026650 dated Nov. 9, 2005.

(Continued)

*Primary Examiner*—Darwin P Erezo
*Assistant Examiner*—Son Dang

(57) ABSTRACT

A reduced deployment force delivery apparatus having an outer sheath with two layers that move relative to one another so as to reduce the deployment force necessary for deploying a stent, stent graft or other intraluminal device.

13 Claims, 2 Drawing Sheets

U.S. PATENT DOCUMENTS

| | | | |
|---|---|---|---|
| 6,380,457 B1 * | 4/2002 | Yurek et al. | 623/1.11 |
| 6,432,080 B2 * | 8/2002 | Pederson et al. | 604/103.07 |
| 6,443,980 B1 * | 9/2002 | Wang et al. | 623/1.11 |
| 6,547,813 B2 * | 4/2003 | Stiger et al. | 623/1.11 |
| 6,565,595 B1 * | 5/2003 | DiCaprio et al. | 623/1.11 |
| 6,669,718 B2 * | 12/2003 | Besselink | 623/1.11 |
| 6,669,719 B2 * | 12/2003 | Wallace et al. | 623/1.12 |
| 6,726,714 B2 * | 4/2004 | DiCaprio et al. | 623/1.11 |
| 6,890,337 B2 * | 5/2005 | Feeser et al. | 606/108 |
| 6,942,682 B2 * | 9/2005 | Vrba et al. | 606/198 |
| 6,949,121 B1 * | 9/2005 | Laguna | 623/1.35 |
| 7,001,423 B2 * | 2/2006 | Euteneuer et al. | 623/1.12 |
| 7,309,349 B2 * | 12/2007 | Jackson et al. | 623/1.11 |
| 2002/0007192 A1 | 1/2002 | Pederson et al. | |
| 2002/0099431 A1 * | 7/2002 | Armstrong et al. | 623/1.11 |
| 2002/0138127 A1 * | 9/2002 | Stiger et al. | 623/1.11 |
| 2003/0033000 A1 * | 2/2003 | DiCaprio et al. | 623/1.11 |
| 2003/0074044 A1 * | 4/2003 | Randby et al. | 623/1.11 |
| 2003/0105508 A1 * | 6/2003 | Johnson et al. | 623/1.11 |
| 2004/0141577 A1 | 7/2004 | Brunn et al. | |
| 2004/0143315 A1 * | 7/2004 | Bruun et al. | 623/1.11 |
| 2004/0193177 A1 * | 9/2004 | Houghton et al. | 606/108 |
| 2005/0049666 A1 * | 3/2005 | Chien et al. | 623/1.11 |
| 2005/0119719 A1 * | 6/2005 | Wallace et al. | 623/1.11 |
| 2006/0030922 A1 * | 2/2006 | Dolan | 623/1.11 |
| 2007/0142892 A1 * | 6/2007 | Dave et al. | 623/1.11 |

FOREIGN PATENT DOCUMENTS

| | | |
|---|---|---|
| WO | WO 96/32078 A1 | 10/1996 |
| WO | 01/78627 A1 | 10/2001 |
| WO | WO 01/78627 A1 | 10/2001 |
| WO | 02/38084 A2 | 5/2002 |
| WO | WO 02/38084 A2 | 5/2002 |

OTHER PUBLICATIONS

European Search Report EP 05 25 4516 dated Nov. 8, 2005.
International Search Report for corresponding patent application No. PCT/US2005/0266.
European Search Report for corresponding patent application No. EP05254516 dated Nov. 8, 2005.
European Search Report for corresponding patent application No. EP 05777469.7 dated Apr. 3, 2009.

* cited by examiner

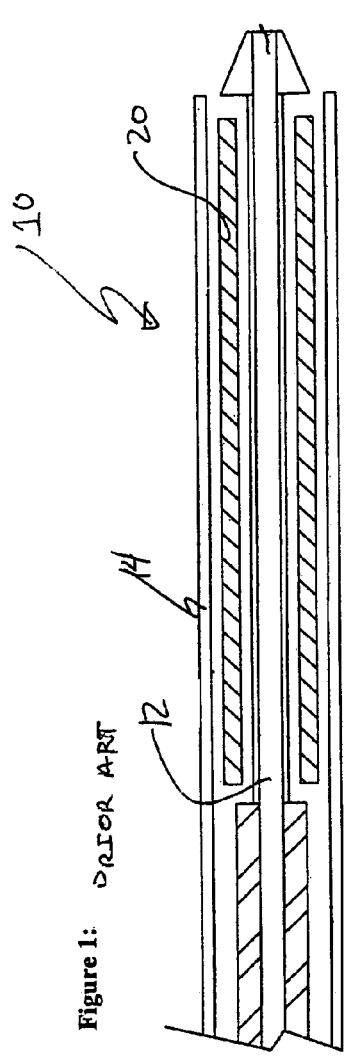
Figure 1: PRIOR ART
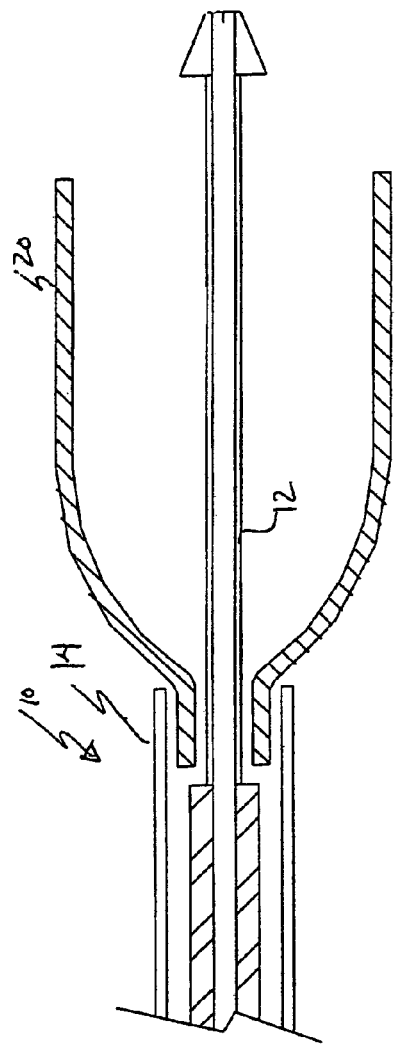
Figure 2 PRIOR ART

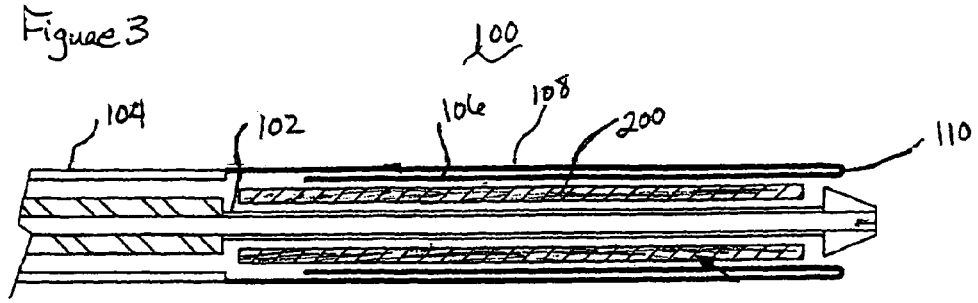
Figure 3
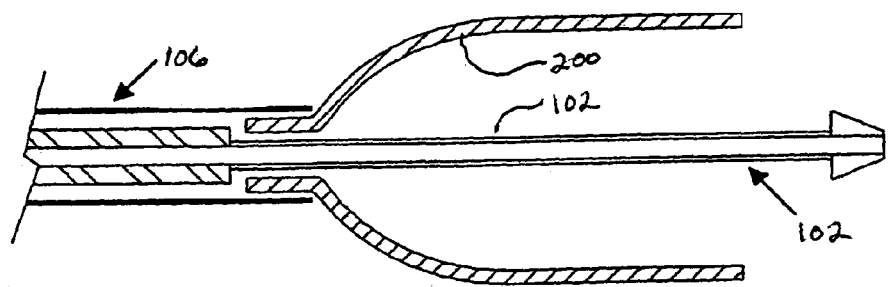
Figure 4
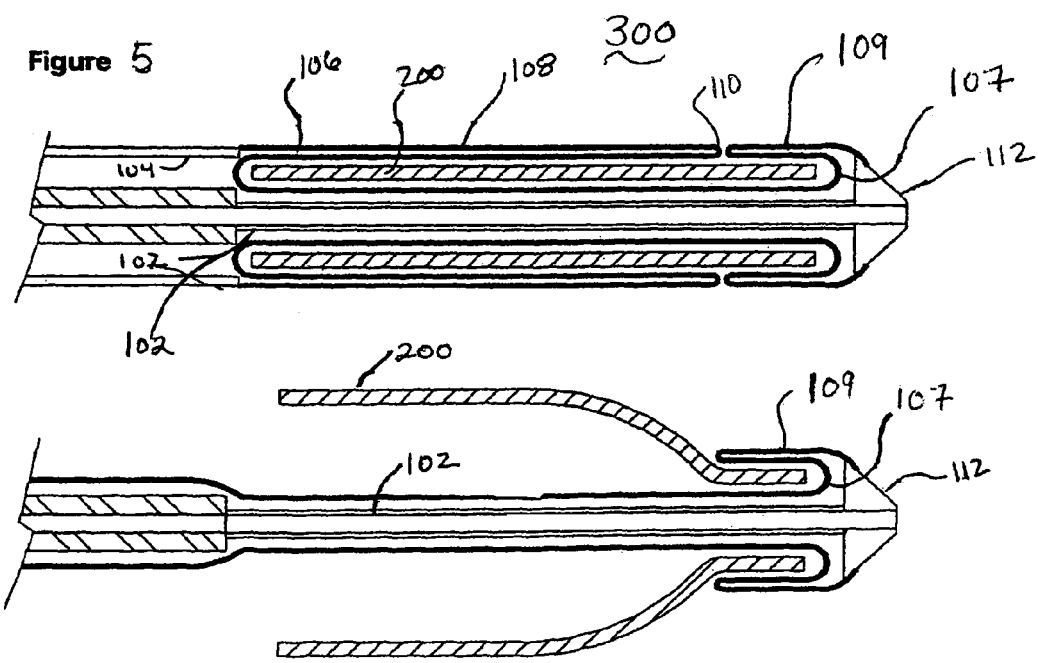
Figure 5
Figure 6

REDUCED DEPLOYMENT FORCE DELIVERY DEVICE

CROSS REFERENCE TO RELATED APPLICATIONS

This application claims the benefit of U.S. Provisional Patent Application Ser. No. 60/591,950 filed Jul. 28, 2004.

BACKGROUND OF THE INVENTION

1. Field of the Invention

The present invention relates to delivery devices, and more particularly, to reduced deployment force delivery devices for self-deploying intraluminal devices.

2. Discussion of the Related Art

An aneurysm is an abnormal dilation of a layer or layers of an arterial wall, usually caused by a systemic collagen synthetic or structural defect. An abdominal aortic aneurysm is an aneurysm in the abdominal portion of the aorta, usually located in or near one or both of the two iliac arteries or near the renal arteries. The aneurysm often arises in the infrarenal portion of the diseased aorta, for example, below the kidneys. A thoracic aortic aneurysm is an aneurysm in the thoracic portion of the aorta. When left untreated, the aneurysm may rupture, usually causing rapid fatal hemorrhaging.

Aneurysms may be classified or typed by their position as well as by the number of aneurysms in a cluster. Typically, abdominal aortic aneurysms may be classified into five types. A Type I aneurysm is a single dilation located between the renal arteries and the iliac arteries. Typically, in a Type I aneurysm, the aorta is healthy between the renal arteries and the aneurysm and between the aneurysm and the iliac arteries.

A Type II A aneurysm is a single dilation located between the renal arteries and the iliac arteries. In a Type II A aneurysm, the aorta is healthy between the renal arteries and the aneurysm, but not healthy between the aneurysm and the iliac arteries. In other words, the dilation extends to the aortic bifurcation. A Type II B aneurysm comprises three dilations. One dilation is located between the renal arteries and the iliac arteries. Like a Type II A aneurysm, the aorta is healthy between the aneurysm and the renal arteries, but not healthy between the aneurysm and the iliac arteries. The other two dilations are located in the iliac arteries between the aortic bifurcation and the bifurcations between the external iliacs and the internal iliacs. The iliac arteries are healthy between the iliac bifurcation and the aneurysms. A Type II C aneurysm also comprises three dilations. However, in a Type II C aneurysm, the dilations in the iliac arteries extend to the iliac bifurcation.

A Type III aneurysm is a single dilation located between the renal arteries and the iliac arteries. In a Type III aneurysm, the aorta is not healthy between the renal arteries and the aneurysm. In other words, the dilation extends to the renal arteries.

A ruptured abdominal aortic aneurysm is presently the thirteenth leading cause of death in the United States. The routine management of abdominal aortic aneurysms has been surgical bypass, with the placement of a graft in the involved or dilated segment. Although resection with a synthetic graft via transperitoneal or retroperitoneal procedure has been the standard treatment, it is associated with significant risk. For example, complications include perioperative myocardial ischemia, renal failure, erectile impotence, intestinal ischemia, infection, lower limb ischemia, spinal cord injury with paralysis, aorta-enteric fistula, and death. Surgical treatment of abdominal aortic aneurysms is associated with an overall mortality rate of five percent in asymptomatic patients, sixteen to nineteen percent in symptomatic patients, and is as high as fifty percent in patients with ruptured abdominal aortic aneurysms.

Disadvantages associated with conventional surgery, in addition to the high mortality rate, include an extended recovery period associated with the large surgical incision and the opening of the abdominal cavity, difficulties in suturing the graft to the aorta, the loss of the existing thrombosis to support and reinforce the graft, the unsuitability of the surgery for many patients having abdominal aortic aneurysms, and the problems associated with performing the surgery on an emergency basis after the aneurysm has ruptured. Further, the typical recovery period is from one to two weeks in the hospital and a convalescence period, at home, ranging from two to three months or more, if complications ensue. Since many patients having abdominal aortic aneurysms have other chronic illnesses, such as heart, lung, liver and/or kidney disease, coupled with the fact that many of these patients are older, they are less than ideal candidates for surgery.

The occurrence of aneurysms is not confined to the abdominal region. While abdominal aortic aneurysms are generally the most common, aneurysms in other regions of the aorta or one of its branches are possible. For example, aneurysms may occur in the thoracic aorta. As is the case with abdominal aortic aneurysms, the widely accepted approach to treating an aneurysm in the thoracic aorta is surgical repair, involving replacing the aneurysmal segment with a prosthetic device. This surgery, as described above, is a major undertaking, with associated high risks and with significant mortality and morbidity.

Over the past five years, there has been a great deal of research directed at developing less invasive, endovascular, i.e., catheter directed, techniques for the treatment of aneurysms, specifically abdominal aortic aneurysms. This has been facilitated by the development of vascular stents, which can and have been used in conjunction with standard or thin-wall graft material in order to create a stent-graft or endograft. The potential advantages of less invasive treatments have included reduced surgical morbidity and mortality along with shorter hospital and intensive care unit stays.

Stent-grafts or endoprostheses are now Food and Drug Administration (FDA) approved and commercially available. Their delivery procedure typically involves advanced angiographic techniques performed through vascular accesses gained via surgical cut down of a remote artery, which may include the common femoral or brachial arteries. Over a guidewire, the appropriate size introducer will be placed. The catheter and guidewire are passed through the aneurysm. Through the introducer, the stent-graft will be advanced to the appropriate position. Typical deployment of the stent-graft device requires withdrawal of an outer sheath while maintaining the position of the stent-graft with an inner-stabilizing device. Most stent-grafts are self-expanding; however, an additional angioplasty procedure, e.g., balloon angioplasty, may be required to secure the position of the stent-graft. Following the placement of the stent-graft, standard angiographic views may be obtained.

Due to the large diameter of the above-described devices, typically greater than twenty French (3F=1 mm), arteriotomy closure typically requires open surgical repair. Some procedures may require additional surgical techniques, such as hypogastric artery embolization, vessel ligation, or surgical bypass in order to adequately treat the aneurysm or to maintain blood flow to both lower extremities. Likewise, some procedures will require additional advanced catheter directed techniques, such as angioplasty, stent placement and embolization, in order to successfully exclude the aneurysm and efficiently manage leaks.

While the above-described endoprostheses represent a significant improvement over conventional surgical techniques, there is a need to improve the endoprostheses, their method of use and their applicability to varied biological conditions. Accordingly, in order to provide a safe and effective alternate means for treating aneurysms, including abdominal aortic aneurysms and thoracic aortic aneurysms, a number of difficulties associated with currently known endoprostheses and their delivery systems must be overcome. One concern with the use of endoprostheses is the prevention of endo-leaks and the disruption of the normal fluid dynamics of the vasculature. Devices using any technology should preferably be simple to position and reposition as necessary, should preferably provide an acute, fluid tight seal, and should preferably be anchored to prevent migration without interfering with normal blood flow in both the aneurysmal vessel as well as branching vessels. In addition, devices using the technology should preferably be able to be anchored, sealed, and maintained in bifurcated vessels, tortuous vessels, highly angulated vessels, partially diseased vessels, calcified vessels, odd shaped vessels, short vessels, and long vessels. In order to accomplish this, the endoprostheses should preferably be highly durable, extendable and re-configurable while maintaining acute and long-term fluid tight seals and anchoring positions.

The market today is populated by devices approximately 20 F and greater requiring the need for a surgical cut-down approach utilizing catheters, guidewires and accessory devices which substantially eliminate the need for open surgical intervention. Although, the cut-down approach significantly reduces the acute complications that often accompany open surgical intervention, the ultimate goal and the market trend, is to reduce delivery system profiles and to be able to perform the procedure of delivering an endoprosthesis percutaneously, as by the Seldinger technique, which eliminates the need for a cut-down procedure.

To accomplish significantly lower profiles of a delivery system, the intraluminal device will typically be crimped tighter, which tends to increase stresses on the sheath. Therefore, there is a need to find some way to minimize the deployment force in order to reduce the risk of damage to the endoprosthesis and/or the delivery system.

SUMMARY OF THE INVENTION

The reduced deployment force delivery device of the various embodiments described herein aims to overcome the limitations associated with currently utilized devices, wherein as referred to herein proximal denotes a direction or location towards an operator and distal denotes a direction or location away from the operator.

In accordance with one embodiment, the reduced deployment force delivery device delivers an intraluminal device to an intended vessel or anatomical passage. The delivery device comprises an inner tube having a proximal region and a distal region, wherein the distal region of the inner tube is configured to receive an intraluminal device such as a stent, stent graft or other intraluminal device. A sheath, having a proximal end and a distal end, is positioned concentrically around at least a portion of the inner tube. The distal end of the sheath comprises an inner layer at least partially covering the intraluminal device and an outer layer. A proximal end of the outer layer being connected to the distal end of the sheath and the inner layer and outer layer being connected to each other at a distal end of each and configured for relative movement therebetween. In this manner, the inner layer is peeled away from the stent, stent graft or other intraluminal device as the sheath is retracted until the inner layer is completely inverted, whereafter the remaining portion of the inner layer is retracted in conventional manner to achieve deployment of the stent, stent graft or intraluminal device.

In another embodiment, the reduced deployment force delivery device delivers an intraluminal device to an intended vessel or anatomical passage, whereby the delivery device comprises an inner tube having a proximal region and a distal region. The distal region of the inner tube is configured to receive an intraluminal device, such as a stent, stent graft or other intraluminal device. A sheath, having a proximal end and a distal end, is positioned concentrically around at least a portion of the inner tube. The distal end of the sheath comprises an outer layer, wherein a proximal end of the outer layer is connected to the distal end of the sheath as in the earlier described embodiment. The outer layer is likewise connected to an inner layer as in the earlier described embodiment. However, the inner layer in this instance proceeds along a portion of the stent, stent graft or intraluminal device to wrap around a proximal end of the stent, stent graft or other intraluminal device and through the lumen of the stent, stent graft or other intraluminal device to a distal end section of the inner layer beyond the distal end of the lumen of the stent, stent graft or intraluminal device. Thereafter, the inner layer returns briefly proximally along a distal portion of the stent, stent graft or intraluminal device before proceeding to connect to a distal tip of the inner tube of the delivery device. In this manner, the proximal end of the stent, stent graft or intraluminal device can be deployed before the distal end thereof by continued retraction of the sheath.

In either of the embodiments described herein, a lubricious material may be provided between the inner and outer layers in order to render movement thereof easier. Likewise, the inner layer in either embodiment may taper from its proximal end to its distal end so as to become larger at its distal end, although the inner layer may also be of constant dimensions.

BRIEF DESCRIPTION OF THE DRAWINGS

The foregoing and other features and advantages of the invention will be apparent from the following, more particular description of preferred embodiments of the invention, as illustrated in the accompanying drawings.

FIG. 1 is a diagrammatic representation of a conventional deployment force delivery system.

FIG. 2 is a diagrammatic representation of a conventional deployment force delivery system with an intraluminal device partially deployed.

FIG. 3 is a diagrammatic representation of an alternate embodiment of a low deployment force delivery system in accordance with the invention.

FIG. 4 is a diagrammatic representation of the alternate embodiment of the deployment force delivery system of FIG. 3 with the intraluminal device partially deployed in accordance with the invention.

FIG. 5 is a diagrammatic representation of another alternate low deployment force delivery system in accordance with the invention.

FIG. 6 is a diagrammatic representation of the alternate embodiment of the deployment force delivery system of FIG. 5 with the intraluminal device partially deployed in accordance with the invention.

DETAILED DESCRIPTION OF THE PREFERRED EMBODIMENTS

Various endoprosthesis assemblies, which include expandable stents and/or stent grafts, have been proposed or developed for use in association with angioplasty treatments and other medical procedures such as aneurysm repair. The endoprosthesis assembly is generally routed via catheter to a treatment site and the stent and/or stent graft is expanded to restore the smooth patency of an anatomical passageway by opening up a blockage or narrowing, or, in the case of a grafted stent, to exclude blood flow to an opening or aneurysm such as in blood vessel or bile duct. A stent is typically cylindrical in shape comprising an expandable open frame. The stent and/or stent graft will typically expand either by itself (self-expanding stents) or will expand upon exertion of an outwardly directed radial force on an inner surface of the stent frame by a balloon catheter or the like. The deployment of a stent or stent graft is substantially the same as is described in detail subsequently.

Accordingly, there is a need for a self-expanding stent, stent graft or intraluminal device delivery system that is able to navigate tortuous passageways, that prevents the stent, stent graft or intraluminal device from becoming embedded therein, and that allows the physician to more easily and accurately deploy the stent, stent graft or intraluminal device within the target area.

Stents, for example, for endovascular implantation into a blood vessel or the like, to maintain or restore the patency of the passageway, have often been deployed percutaneously to minimize the invasiveness associated with surgical exposure of the treatment site during coronary artery bypass. Percutaneous deployment is initiated by an incision into the vascular system of the patient, typically into the femoral artery. A tubular or sheath portion of an introducer is inserted through the incision and extends into the artery. The introducer has a central lumen which provides a passageway through the patient's skin and artery wall into the interior of the artery. An outwardly tapered hub portion of the introducer remains outside the patient's body to prevent blood from leaking out of the artery along the outside of the sheath. The introducer lumen includes a valve to block blood flow out of the artery through the introducer passageway. A distal end of a guide wire is passed through the introducer passageway into the patient's vasculature. The guide wire is threaded through the vasculature until the inserted distal end extends just beyond the treatment site. The proximal end of the guide wire extends outside the introducer.

For endovascular deployment, a stent, in an unexpanded or constricted configuration, is crimped onto a deflated balloon portion of a balloon catheter. The balloon portion is normally disposed near a distal end of the balloon catheter. The catheter has a central lumen extending its entire length. The distal end of the balloon catheter is threaded onto the proximal end of the guide wire. The distal end of the catheter is inserted into the introducer lumen and the catheter is pushed along the guide wire until the stent reaches the treatment site. At the treatment site, the balloon is inflated causing the stent to radially expand and assume an expanded configuration. When the stent is used to reinforce a portion of the blood vessel wall, the stent is expanded such that its outer diameter is approximately ten percent to twenty percent larger than the inner diameter of the blood vessel at the treatment site, effectively causing an interference fit between the stent and the blood vessel that inhibits migration of the stent. The balloon is deflated and the balloon catheter is withdrawn from the patient's body. The guide wire is similarly removed. Finally, the introducer is removed from the artery.

An example of a commonly used stent is given in U.S. Pat. No. 4,733,665 filed by Palmaz on Nov. 7, 1985. Such stents are often referred to as balloon expandable stents. Typically the stent is made from a solid tube of stainless steel. Thereafter, a series of cuts are made in the wall of the stent. The stent has a first smaller diameter which permits the stent to be delivered through the human vasculature by being crimped onto a balloon catheter. The stent also has a second or expanded diameter. The expanded diameter is achieved through the application, by the balloon catheter positioned in the interior of the tubular shaped member, of a radially outwardly directed force.

However, such "balloon expandable" stents are often impractical for use in some vessels such as superficial arteries, like the carotid artery. The carotid artery is easily accessible from the exterior of the human body. A patient having a balloon expandable stent made from stainless steel or the like, placed in their carotid artery might be susceptible to sever injury through day to day activity. A sufficient force placed on the patient's neck, such as by falling, could cause the stent to collapse, resulting in injury to the patient. In order to prevent this, self-expanding stents have been proposed for use in such vessels. Self-expanding stents act similarly to springs and will recover to their expanded or implanted configuration after being crushed.

One type of self-expanding stent is disclosed in U.S. Pat. No. 4,665,771. The disclosed stent has a radially and axially flexible, elastic tubular body with a predetermined diameter that is variable under axial movement of ends of the body relative to each other and which is composed of a plurality of individually rigid but flexible and elastic thread elements defining a radially self-expanding helix. This type of stent is known in the art as a "braided stent" and is so designated herein. Placement of such stents in a body vessel can be achieved by a device which comprises an outer catheter for holding the stent at its distal end, and an inner piston which pushes the stent forward once it is in position.

Other types of self-expanding stents use alloys such as Nitinol (Ni—Ti alloy), which have shape memory and/or superelastic characteristics in medical devices which are designed to be inserted into a patient's body. The shape memory characteristics allow the devices to be deformed to facilitate their insertion into a body lumen or cavity and then be heated within the body so that the device returns to its original shape. Superelastic characteristics on the other hand generally allow the metal to be deformed and restrained in the deformed condition to facilitate the insertion of the medical device containing the metal into a patient's body, with such deformation causing the phase transformation. Once within the body lumen the restraint on the superelastic member can be removed, thereby reducing the stress therein so that the superelastic member can return to its original un-deformed shape by the transformation back to the original phase.

Alloys having shape memory/superelastic characteristics generally have at least two phases. These phases are a martensite phase, which has a relatively low tensile strength and which is stable at relatively low temperatures, and an austenite phase, which has a relatively high tensile strength and which is stable at temperatures higher than the martensite phase.

When stress is applied to a specimen of a metal, such as Nitinol, exhibiting superelastic characteristics at a temperature above which the austenite is stable (i.e. the temperature at which the transformation of martensite phase to the austenite phase is complete), the specimen deforms elastically until it reaches a particular stress level where the alloy then undergoes a stress-induced phase transformation from the austenite phase to the martensite phase. As the phase transformation proceeds, the alloy undergoes significant increases in strain but with little or no corresponding increases in stress. The strain increases while the stress remains essentially constant until the transformation of the austenite phase to the martensite phase is complete. Thereafter, further increase in stress is necessary to cause further deformation. The martensitic metal first deforms elastically upon the application of additional stress and then plastically with permanent residual deformation.

If the load on the specimen is removed before any permanent deformation has occurred, the martensitic specimen will elastically recover and transform back to the austenite phase. The reduction in stress first causes a decrease in strain. As stress reduction reaches the level at which the martensite phase transforms back into the austenite phase, the stress level in the specimen will remain essentially constant (but substantially less than the constant stress level at which the austenite transforms to the martensite) until the transformation back to the austenite phase is complete, i.e. there is significant recovery in strain with only negligible corresponding stress reduction. After the transformation back to austenite is complete, further stress reduction results in elastic strain reduction. This ability to incur significant strain at relatively constant stress upon the application of a load and to recover from the deformation upon the removal of the load is commonly referred to as superelasticity or pseudoelasticity. It is this property of the material which makes it useful in manufacturing tube cut self-expanding stents. The prior art makes reference to the use of metal alloys having superelastic characteristics in medical devices which are intended to be inserted or otherwise used within a patient's body. See for example, U.S. Pat. No. 4,665,905 to Jervis and U.S. Pat. No. 4,925,445 to Sakamoto et al.

Designing delivery systems for delivering self-expanding stents has proven difficult. One example of a prior art self-expanding stent delivery system is shown in U.S. Pat. No. 4,580,568 to Gianturco. This patent discloses a delivery apparatus which uses a hollow sheath, like a catheter. The sheath is inserted into a body vessel and navigated therethrough so that its distal end is adjacent the target site. The stent is then compressed to a smaller diameter and loaded into the sheath at the sheath's proximal end. A cylindrical flat end pusher, having a diameter almost equal to the inside diameter of the sheath is inserted into the sheath behind the stent. The pusher is then used to push the stent from the proximal end of the sheath to the distal end of the sheath. Once the stent is at the distal end of the sheath, the sheath is pulled back, while the pusher remains stationary, thereby exposing the stent and allowing it to expand within the vessel.

However, delivering the stent through the entire length of the catheter may cause many problems, including possible damage to a vessel or the stent during its travel. In addition, it is often difficult to design a pusher having enough flexibility to navigate through the catheter, but also enough stiffness to push the stent out of the catheter. Therefore, it was determined that pre-loading the stent into the distal and of the catheter, and then delivering the catheter through the vessel to the target site may be a better approach. In order to ensure proper placement of the stent within catheter, it is often preferred that the stent be pre-loaded at the manufacturing site. Except this in itself has posed some problems. Because the catheter exerts a significant force on the self-expanding stent, which keeps it from expanding, the stent may tend to become embedded within the wall of the catheter. When this happens, the catheter has difficulty sliding over the stent during delivery. This situation can result in the stent becoming stuck inside the catheter, or could damage the stent during delivery.

Another example of a prior art self-expanding stent delivery system is given in U.S. Pat. No. 4,732,152 to Wallsten et al. This patent discloses a probe or catheter having a self-expanding stent pre-loaded into its distal end. The stent is first placed within a flexible hose and compressed before it is loaded into the catheter. When the stent is at the delivery site the catheter and hose are withdrawn over the stent so that it can expand within the vessel. However, withdrawing the flexible hose over the stent during expansion could also cause damage to the stent.

Accordingly, there is a need for a self-expanding stent, stent graft or intraluminal device delivery system that is able to navigate tortuous passageways, that prevents the stent, stent graft or intraluminal device from becoming embedded therein, and that allows the physician to more easily and accurately deploy the stent, stent graft or intraluminal device within the target area.

FIGS. 1 and 2 illustrate a partial diagrammatic representation of a conventional intraluminal device delivery system 10 at various stage of deployment of the intraluminal device. FIG. 1, for example, shows the system 10 is generally comprised of an inner tube 12 and an outer sheath 14. The inner tube 12 includes a guidewire lumen through which a guidewire (not shown) is deployed to navigate to a target site. A stent, or other intraluminal device, is positioned over a distal end of the inner tube 12 within the sheath 14 until the targeted site has been reached. Thereafter, as shown in FIG. 2, the sheath 14 is retracted to deploy the stent, or other intraluminal device. In FIG. 2, the stent, or other intraluminal device, 20 is shown as partially deployed, for example. Once the stent, or other intraluminal device, 20 is fully deployed distally to proximally by the continued retraction of the sheath, the components comprising the delivery system 10 are retracted.

Referring to FIGS. 3 and 4, there is illustrated an alternate embodiment of a delivery device in accordance with the invention. For ease of explanation, only the distal region of the device is illustrated as the proximal region may be substantially similar to conventional delivery devices. The reduced deployment force delivery device 100 of FIGS. 3 and 4 comprises an inner tube or shaft 102 and an outer sheath 104. The inner tube or shaft 102 includes a guidewire lumen. A stent, stent graft or other intraluminal device 200 is positioned over the distal end of the inner tube or shaft 102 and held in position by at least a portion of the inner layer 106, the outer layer 108, the outer sheath 104, or some combination thereof. The distal end of the outer sheath 104 is connected to a proximal end of an outer layer 108, which in turn connects at its distal end to an inner layer 106 via a connector 110. In this embodiment, the connector 110 is simply a folded region between the inner and outer layers 106, 108. However, the connector 110 may comprise any suitable device for allowing relative movement between the inner and outer layers 106, 108 as described in detail subsequently. The connector 110 may be a bonded region, for example, that connects the inner layer 106 and the outer layer 108 comprised of similar or dissimilar materials. Alternatively, the outer sheath 104 could extend distally so as to comprise the outer layer and connect to the inner layer 106 via the connector 110. The inner tube or shaft 102 and the outer sheath 104 may comprise any suitable, biocompatible materials utilized in delivery catheters. For example, the inner shaft 102 may comprise high density polyethylene and the outer sheath 104 may comprise braided Nylon™. The inner and outer layers may comprise any suitable material, and preferably comprise a very supple but strong material such as woven Dacron™, woven Dyneema HDPE, ePTFE, or some combination thereof. However, as the artisan will readily appreciate, the inner and outer layers may comprise materials other than those specifically identified herein. A lubricious material may be provided between the inner layer and the outer layer to aid relative movement therebetween. The inner layer may be a constant dimenion or may taper distally to a larger dimension at its distal end.

In operation, the physician retracts the outer sheath 104 to deploy the stent, stent graft or intraluminal device 200. Upon retraction of the outer sheath 104, the sheath 104 pulls the outer layer 108 which then inverts the inner layer 106 to expose the stent, stent graft or intraluminal device 200. As illustrated in FIG. 4, once the inner layer 106 is completely inverted, the remaining portion of the stent, stent graft or intraluminal device 200 is deployed in the usual fashion.

FIGS. 5 and 6 illustrate another alternate embodiment of a reduced deployment force delivery device 300 that allows for the most distal portion of the stent, stent graft or intraluminal device 200 to be deployed last, as may be the case for an abdominal aortic aneurysm repair stent graft device that comprises distal barbs. In this embodiment, a proximal end of a first outer layer 108 is connected to the distal end of the sheath 104 and a distal end of the first outer layer 108 is connected to the inner layer 106 as before. In this embodiment however, the inner layer 106 further proceeds to wrap around a proximal end of the stent, stent graft or intraluminal device 200 and through the lumen thereof to a distal end section 107 of the inner layer 106. The distal end section 107 of the inner layer 106 then proceeds proximally along a distal portion of the stent, stent graft or intraluminal device 200, becoming a second outer layer 109, before attaching to the distal tip 112 of the inner tube 102. In this manner, the stent, stent graft or intraluminal device 200 is deployed by retracting the first outer layer 108, followed by retraction of the inner layer 106 and its distal end section 107, the second outer layer 109, and continued retraction of the sheath 104. That is, until the distal end section 107 of the inner layer 106 is uncurled, as by continuous retraction of the sheath 104, the distal end of the stent or stent graft remains unexpanded as illustrated in FIG. 6. Of course, the outer sheath 104 could comprise the first outer layer portion and connect to the inner layer 106 via the connector 110.

In each of these embodiments, the inner layer may be constant, may taper distally so as to be larger at its proximal end than at its distal end, or may taper variably between its proximal and distal ends, whereby the tapering may allow smoother and easier deployment of the stent, stent graft or intraluminal device. In addition, at least one of the inner and outer layers may be coated with a lubricious material to enhance deployment of the stent, stent graft or intraluminal device as well. Further, the inner layer and the outer layer of each embodiment may be comprised of similar materials as identified herein, although the artisan will readily appreciate that other materials of similar qualities and characteristics may also be used other than those identified herein.

Although shown and described is what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope for the appended claims.

What is claimed is:

1. A reduced deployment force delivery device for intraluminal devices comprising:
    an inner tube having a proximal region, a distal region and a distal tip, the distal region configured to receive a self-expanding intraluminal device having proximal and distal ends and a lumen therethrough;
    a sheath having a proximal end and a distal end, the sheath mounted concentrically around the inner tube;
    a first outer layer having a proximal end and a distal end, the proximal end of the first outer layer is connected to a the distal end of the sheath;
    a second outer layer having a proximal end and a distal end, the distal end being connected to the distal tip of the inner tube; and
    an inner layer having a first end and a second end, the first end being connected to a distal end of the first outer layer at a folded region and configured to pass along a first portion of the outer surface of the self-expanding intraluminal device, wrapping around the proximal end of the self-expanding intraluminal device and passing through the lumen of the entire self-expanding intraluminal device, wrapping around the distal end of the self-expanding intraluminal device and proceeding proximally over a second portion of the outer surface of the self-expanding intraluminal device and connecting to the proximal end of the second outer layer at a folded region, wherein the reduced deployment force device is configured to release the proximal end of the self-expanding intraluminal device while maintaining the distal end of the self expanding intraluminal device in a compressed state under the second outer layer until the sheath is fully retracted.

2. The reduced deployment force delivery device of claim 1, further comprising a lubricious coating between the inner layer and the first outer layer portion and between the distal end section of the inner layer and the second outer layer portion.

3. The reduced deployment force delivery device of claim 1, wherein the inner layer tapers so as to be larger at its proximal end.

4. The reduced deployment force delivery device of claim 1, wherein the inner layer tapers variably between its proximal and distal ends.

5. The reduced deployment force delivery device of claim 1, wherein the inner layer, the distal end section thereof, the first outer layer and the second outer layer are comprised of woven Dacron.

6. The reduced deployment force delivery device of claim 1, wherein the inner layer, the distal end section thereof, the first outer layer and the second outer layer are comprised of woven Dyneema HDPE.

7. The reduced deployment force delivery device of claim 1, wherein the inner layer, the distal end section thereof, the first outer layer and the second outer layer are comprised of ePTFE.

8. The reduced deployment force delivery device of claim 1, wherein the inner layer, the distal end section thereof, the first outer layer and the second outer layer are comprised of a combination of woven Dacron and woven Dyneema HDPE.

9. The reduced deployment force delivery device of claim 1, wherein the inner layer and the first outer layer are connected by a folded region therebetween.

10. The reduced deployment force delivery device of claim 1, wherein the inner layer and the second outer layer are connected by a folded region therebetween.

11. The reduced deployment force delivery device of claim 1, wherein the inner layer and the first outer layer are connected by a bonded region therebetween.

12. The reduced deployment force delivery device of claim 1, wherein the distal end section of the inner layer and the second outer layer are connected by a bonded region therebetween.

13. The reduced deployment force delivery device of claim 1, wherein the sheath extends distally to comprise the first outer layer and connects to the inner layer via a connector.

* * * * *